United States Patent [19]

Jenck

[11] Patent Number: 4,539,424

[45] Date of Patent: Sep. 3, 1985

[54] PREPARATION OF LINEAR ESTERS BY CARBONYLATION OF MONOOLEFINS

[75] Inventor: Jean Jenck, Chalampe, France

[73] Assignee: Rhone-Poulenc Chimie De Base, Courbevoie, France

[21] Appl. No.: 543,478

[22] Filed: Oct. 19, 1983

[30] Foreign Application Priority Data

Oct. 19, 1982 [FR] France ................. 82 17663

[51] Int. Cl.$^3$ .............................................. C07C 67/38
[52] U.S. Cl. ..................... 560/204; 502/155; 502/171; 560/114; 560/122; 560/123; 560/124; 560/127; 560/180; 560/192; 560/193; 560/226; 560/228; 560/232
[58] Field of Search ............... 560/204, 193, 192, 180, 560/226, 228, 232, 114, 127, 122, 123, 124; 502/171, 155

[56] References Cited

U.S. PATENT DOCUMENTS

| | | | |
|---|---|---|---|
| 3,397,226 | 8/1968 | Fenton | 560/204 X |
| 3,437,676 | 4/1969 | von Kutepow et al. | 560/204 X |
| 3,507,891 | 4/1970 | Hearne et al. | 560/204 X |
| 3,856,832 | 12/1974 | Ethyl Corp. | 560/204 X |

*Primary Examiner*—Natalie Trousof
*Assistant Examiner*—Vera C. Clarke
*Attorney, Agent, or Firm*—Burns, Doane, Swecker & Mathis

[57] ABSTRACT

Linear esters, e.g., alkyl adipates, are facilely prepared by reacting an alcohol and carbon monoxide with a monoolefin, in the presence of cobalt, optionally hydrogen, and a tertiary nitrogen base, and in a reaction solvent which comprises a 5- or 6-membered monoheterocycle containing from 1 to 3 identical or different, non-adjacent oxygen and divalent sulfur heteroatoms, with the proviso that such heterocycle can also contain from one to two carbon-carbon double bonds, and, if a 5-membered heterocycle, can also contain a nitrogen heteroatom separated from an oxygen or sulfur heteroatom by at least one ring carbon atom and linked to one of the adjacent carbon atoms by a double bond.

20 Claims, No Drawings

PREPARATION OF LINEAR ESTERS BY CARBONYLATION OF MONOOLEFINS

BACKGROUND OF THE INVENTION

1. Field of the Invention

The present invention relates to the preparation of linear esters by the carbonylation of monoolefinic compounds, namely, by reacting carbon monoxide and an alcohol with compounds containing but a single olefinic double bond.

The invention more specifically relates to the preparation of alkyl adipates by the carbonylation of alkyl pentenoates.

2. Description of the Prior Art

It is well known to this art, from *Bulletin of the Chemical Society of Japan*, 46, pages 526 and 527 (1973), that a mixture containing dialkyl esters and, in particular, an alkyl adipate is obtained by reacting carbon monoxide and an alcohol with an alkyl pent-3-enoate, under high pressure and at high temperature, in the presence of cobalt carbonyl and a heterocyclic aromatic nitrogen base. However, the industrial-scale development of a technique of this type, the value of which is not contested in principle, is greatly jeopardized not only by reason of the poor efficacy of the catalyst system, but also by reason of the considerable proportion of alkyl pentanoate formed, even though the reaction is carried out in the absence of hydrogen.

Furthermore, those skilled in this art are well aware that the presence of small amounts of hydrogen in the reaction medium tends to increase the efficacy of cobalt-based catalysts in processes for the synthesis of esters by reacting an alcohol and carbon monoxide with an olefinic compound.

It has nevertheless also been found that, in the majority of cases, the aforenoted favorable effect associated with the presence of small amounts of hydrogen is accompanied by an adverse influence on the process selectivity in respect of linear esters, these being the specific target products.

In fact, it is observed that the presence of hydrogen not only tends to increase the proportion of hydrogenation products in the reaction mixture, but is also capable of reducing the proportion of linear ester in the esters formed.

This adverse effect severely adversely affects the economics of these processes insofar as the utilization of the branched esters and the hydrogenation products is uncertain or even non-existent. This is the case, in particular, of the branched diesters and the alkyl pentanoates produced during the carbonylation of alkyl pentenoates. Indeed, as these products are in practice destroyed, their formation amounts to an intolerable loss of starting material. Furthermore, hydrogen can be formed in situ from the traces of water which may be present in technical-grade reactants, according to the well-known reaction:

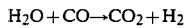

$$H_2O + CO \rightarrow CO_2 + H_2$$

For obvious economic reasons, it would be desirable to be able to use technical-grade carbon monoxide containing hydrogen, without this detracting from process selectivity in respect of linear esters, these being the target esters. It would also be desirable, for the same reasons, to be able to use reactants containing trace amounts of water, without this leading to a loss of starting material.

SUMMARY OF THE INVENTION

Accordingly, a major object of the present invention is the provision of a surprisingly and unexpectly improved process for the preparation of linear carboxylic acid esters by reacting an alcohol and carbon monoxide with a compound containing but a single olefinic double bond, in the presence of cobalt and a tertiary nitrogen base, provided that the reaction is carried out in a solvent selected from among heterocyclic compounds containing a single heterocyclic ring; the said heterocyclic ring, which is formed of 5 or 6 members, contains from 1 to 3 identical or different, non-adjacent heteroatoms selected from oxygen and divalent sulfur, and can contain, if appropriate, one or two carbon-carbon double bonds, it being possible for a 5-membered ring to also contain a nitrogen heteroatom separated from an oxygen or sulfur heteroatom by at least one carbon atom of the ring and joined to one of the adjacent carbon atoms by a double bond.

DETAILED DESCRIPTION OF THE INVENTION

More particularly according to the present invention, carbon monoxide and an alcohol R—OH are reacted with a compound of the formula $R_1CH=CHR_2$, in which:

(i) $R_1$ and $R_2$, which are identical or different, represent hydrogen or an alkyl radical having up to 20 carbon atoms, which can be substituted by 1 or 2 chlorine atoms or alkoxy groups containing up to 4 carbon atoms;

(ii) it also being possible for $R_1$ to represent a radical —$CH_2)_p$COOH, —$CH_2)_p$COOR$_3$ or —$CH_2)_p$CN, in which p is an integer which is equal to at most 6 and can be zero, and $R_3$ represents an alkyl radical containing up to 12 carbon atoms, it also being possible for one to two methylene groups to bear an alkyl substituent having at most 4 carbon atoms;

(iii) it also being possible for $R_1$ and $R_2$ to together form a single divalent radical —$CH_2)_q$ containing, if appropriate, one or two alkyl substituents having up to 4 carbon atoms, q being an integer ranging from 3 to 6 inclusive; and (iv) R is an alkyl radical containing up to 12 carbon atoms, which is optionally substituted by one or two hydroxyl groups, a cycloalkyl radical having from 5 to 7 carbon atoms, an aralkyl radical having from 7 to 12 carbon atoms or a phenyl radical.

The starting materials which can be carbonylated according to the process of the present invention are, therefore, compounds containing but a single internal or terminal olefinic bond; these compounds more specifically contain from 3 to 20 carbon atoms.

The subject process yields saturated esters, namely, compounds which contain on the one hand a carboxylate group (—COOR) and on the other hand one hydrogen atom more than the starting material. Predominant among such esters is the compound whose carboxylate group (—COOR) is located in the terminal position on the main chain or backbone of the starting material.

A first category of starting materials which are more especially preferred has the formula:

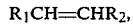

$R_1CH=CHR_2$, in which $R_1$ and $R_2$, which are identical or different, represent hydrogen or an alkyl radical having up to 10 carbon atoms, or together form a single divalent radical —$(CH_2)_q$, with q being as above-defined, it being possible, if appropriate, for the said radical to contain 1 or 2 methyl substituents. Propylene, but-1-ene, but-2-ene, hexenes, octenes and dodec-1-ene are representative examples of these compounds.

A second category of starting materials which are more especially preferred are compounds of the formula:

$$R_1CH=CHR_2,$$

in which $R_1$ represents a radical —$(CH_2)_pCOOR_3$, p and $R_3$ being as above-defined, it being possible for one to two methylene groups to bear an alkyl substituent having up to 4 carbon atoms, and $R_2$ represents hydrogen or an alkyl radical having up to 4 carbon atoms.

Among the compounds of this type, alkyl pentenoates are very especially preferred because they make it possible to prepare alkyl adipates, which are intermediates of adipic acid.

The present process requires the use of an alcohol of the formula ROH, with R being as above-defined.

Exemplary of alcohols which can be used within the scope of the present invention, representative are methanol, ethanol, isopropanol, n-propanol, tert.-butanol, n-hexanol, cyclohexanol, 2-ethylhexan-1-ol, dodecan-1-ol, ethylene glycol, hexane-1,6-diol, benzyl alcohol, phenylethyl alcohol and phenol.

It is preferred to use an alkanol having at most 4 carbon atoms; methanol and ethanol are thus especially suitable for carrying out the present process.

The alcohol and the monoolefinic compound can be used in stoichiometric amounts. However, it is preferred to use an excess of alcohol in a proportion of 1 to 10 mol, or more preferably 2 to 5 mol, of alcohol per mol of monoolefinic compound.

The reaction is carried out in the presence of cobalt. Any source of cobalt capable of reacting with carbon monoxide in the reaction medium to give cobalt carbonyl complexes in situ can be used within the scope of the process according to the invention.

Examples of typical sources of cobalt are finely divided cobalt metal, inorganic salts such as cobalt nitrate or carbonate, and organic salts, in particular carboxylates. Cobalt carbonyls or hydrocarbonyls can also be employed; dicobalt octacarbonyl, for example, is suitable for carrying out the subject process.

The molar ratio of the monoolefinic compound to the cobalt advantageously ranges from 10 to 1,000. Such ratio is preferably fixed at a value ranging from 20 to 300.

The process according to the present invention also requires the presence of a tertiary nitrogen base having a $pK_a$ advantageously ranging from 3 to 10.

Consistent herewith, advantageously employed are 5- or 6-membered nitrogen heterocycles which can contain one or two substituents selected from among alkyl or alkoxy groups having up to 4 carbon atoms, the hydroxyl group and halogen atoms, which optionally contain 2 or 3 double bonds and which can furthermore, if appropriate, be fused to a benzene nucleus, with the proviso that the ring members adjacent to the nitrogen heteroatom are neither substituted nor common to two rings.

6-Membered nitrogen heterocycles having a $pK_a$ ranging from 4 to 7, in particular pyridine, 4-picoline, isoquinoline and 3,5-lutidine, are more particularly preferred for carrying out the process according to the invention.

The amount of tertiary nitrogen base employed is typically such that the molar ratio of N/Co ranges from 1 to 50. To carry out the invention with especially good results, this ratio advantageously ranges from 2 to 25.

One of the essential characteristics of the present invention is the use of a solvent selected from among heterocyclic compounds containing a single heterocyclic ring; the said heterocyclic ring, which is formed of 5 or 6 members, contains from 1 to 3 identical or different, non-adjacent heteroatoms selected from oxygen and divalent sulfur, and can contain, if appropriate, one or two carbon-carbon double bonds, it also being possible for a 5-membered ring to contain a nitrogen heteroatom separated from an oxygen or sulfur heteroatom by at least one carbon atom of the ring and joined to one of the adjacent carbon atoms by a double bond.

Of course, the heterocyclic ring can contain from 1 to 4, preferably 1 or 2, carbon atoms substituted by one or two groups which do not interfere with the other components of the reaction medium, and the size of which is sufficiently small not to create excessive steric hindrance around the heteroatom (or heteroatoms) of the ring. Permissible substituents correspond to the formula R'—Y—, in which Y represents a valence bond, an oxygen atom, a sulfur atom or a carbonyl group and R represents an alkyl, aralkyl or aryl radical containing up to 10 carbon atoms.

Likewise, one or two pairs of adjacent carbon atoms of the heterocyclic ring can each be included in a benzene or naphthalene nucleus joined to the heterocyclic ring.

Representative examples of heterocyclic compounds suitable for carrying out the present invention are: tetrahydrofuran, 2-methyltetrahydrofuran, 2-ethyltetrahydrofuran, 2-phenyltetrahydrofuran, 2,3-dihydrobenzofuran, furan, 2-methylfuran, 2-ethylfuran, 2-phenylfuran, benzofuran, dibenzofuran, tetrahydrothiophene, 2-methyltetrahydrothiophene, 2-phenyltetrahydrothiophene, 2,3-dihydrobenzothiophene, thiophene, 2-methylthiophene, 2-phenylthiophene, benzothiophene, naphthothiophene, dibenzothiophene, benzodioxole, 1,3-benzodithiolane, 1,3-benzoxathiolane, oxazole, 2,5-dimethyloxazole, 2,5-diphenyloxazole, benzoxazole, thiazole, 2,4-diphenylthiazole, benzothiazole, tetrahydropyran, chromane, isochromane, xanthene, 1,3-dioxane, 1,4-dioxane, 1,4-benzodioxane, 1,3,5-trioxane, 2,4,6-trimethyl-1,3,5-trioxane, thian, 1,3-dithian, 1,4-dithian, 1,4-benzodithian, thianthrene, 1-oxa-3-thian, 1-oxa-4-thian, phenoxathine and 1,3,5-trithian.

Preferably, an unsubstituted heterocyclic compound will be used insofar as the beneficial influence observed seems to decrease with the degree of hindrance around the heteroatom (or heteroatoms) of the ring.

A first category of heterocyclic compounds which are particularly suitable for carrying out the present invention consists of heterocyclic compounds which contain exclusively one (or more) sulfur heteroatoms.

A second category of heterocyclic compounds which are particularly suitable for carrying out the subject process consists of heterocyclic compounds containing 6 members and at least 2 heteroatoms which are of the same type and which are selected from oxygen and divalent sulfur.

To carry out the present invention with especially good results, the heterocyclic compound (solvent for the reaction) will be selected from among thiophene, tetrahydrothiophene, furan, tetrahydrofuran, 1,4-dioxane, 1,4-dithian and trithian.

The amount of solvent, which influences the selectivity of the reaction, will generally be more than 20% (by weight) of the initial reaction mixture, and, to carry out the present process with especially good results, it will range from 30 to 60% (by weight) of the said mixture.

In one preferred embodiment of the present invention, the reaction is also carried out in the presence of hydrogen. Within the scope of this embodiment, the hydrogen will represent at least 0.1% (by volume) of the carbon monoxide, but will not exceed 3% (by volume). Preferably, the proportion of hydrogen will represent 0.2 to 2% (by volume) of the carbon monoxide.

Of course, although the hydrogen can conveniently be introduced into the reaction medium in the form of a mixture with the carbon monoxide, it can also be fed in separately.

The reaction is advantageously carried out in the liquid phase at a temperature above 120° C., there being no advantage in exceeding 200° C., and under a carbon monoxide pressure which is at least 50 bars and which can be as much as 1,000 bars. The reaction is preferably carried out at a temperature on the order of 130° to 180° C. and under a carbon monoxide pressure on the order of 100 to 300 bars.

Of course, the optimum pressure and temperature conditions will be the more severe, the less reactive the starting material, and this arises, in particular, when the degree of steric protection of the double bond increases.

In addition to hydrogen, the carbon monoxide used can contain impurities such as carbon dioxide, methane and nitrogen. As hereinbefore mentioned, a more particularly valuable application of the process according to the present invention is the synthesis of diesters from alkyl pentenoates. In general, an alkyl pent-3-enoate is used, although alkyl pent-2-enoates, alkyl pent-4-enoates and mixtures of alkyl pentenoates can be used. Also within the scope of this invention, it is preferred to select the alcohol (co-reactant) corresponding to the alkyl radical of the starting material ester, the alkyl radical advantageously having up to 4 carbon atoms. Good results are obtained when starting from one or more of the following pairs of reactants: methyl pentenoate and methanol, or ethyl pentenoate and ethanol.

Upon completion of the reaction, or when the desired degree of conversion has been attained, the target linear ester is recovered by any suitable means, for example, by distillation or liquid/liquid extraction.

In order to further illustrate the present invention and the advantages thereof, the following specific examples are given, it being understood that same are intended only as illustrative and in nowise limitative.

EXAMPLES

The following conventions are used in the examples below.

The products formed do not include the compounds resulting from position isomerism of the olefinic double bond.

The products formed are essentially the diesters and the alkyl pentanoate, the latter resulting from the hydrogenation of the starting ester.

$A$ denotes the activity expressed in mol of products formed per hour and per gram atom of cobalt.

$X$ (%) denotes the number of mol of diesters per 100 mol of products formed.

$Y$ (%) denotes the number of mol of alkyl adipates per 100 mol of products formed.

$Z$ (%) denotes the number of mol of alkyl pentanoate per 100 mol of products formed.

EXAMPLES 1 TO 18

Control Experiments (a) to (k)

A series of experiments was carried out according to the following procedure:

Methyl pent-3-enoate ($P_3$), methanol, dicobalt octacarbonyl (DCOC), isoquinoline and, if appropriate, a solvent were introduced into a 125 ml stainless steel autoclave purged under argon.

The autoclave was then purged with a stream of carbon monoxide, if appropriate containing hydrogen. The autoclave was then brought to the temperature T under a pressure P. After a given reaction time (designated by t and expressed in hours) at this temperature, the autoclave was cooled and degassed. The reaction mixture was analyzed by gas chromatography. The particular conditions and the results obtained are reported respectively in Tables I(A) and I(B) below:

In Table I(A), the ratios of MeOH/$P_3$, $P_3$/Co and N/Co respectively denote the molar ratio of the methanol to the pent-3-enoate, the ratio of the number of mol of pent-3-enoate to the number of gram atoms of cobalt, and the ratio of the number of mol of isoquinoline to the number of gram atoms of cobalt.

In Table I(B):

THP denotes tetrahydropyran
THT denotes tetrahydrothiophene
THF denotes tetrahydrofuran
2-MeF denotes 2-methylfuran
DBF denotes dibenzofuran.

Control experiments (a) to (d) clearly reflect that, in the absence of solvent, the presence of hydrogen results in an increase in the efficacy of the cobalt-based catalyst and in a considerable drop in the selectivity in respect of dimethyl adipate.

Examples 1 to 18 reflect that the simultaneous presence of a solvent according to the invention and hydrogen makes it possible to obtain dimethyl adipate selectively and efficiently.

EXAMPLE 19

Using the autoclave and the procedure described above, an experiment was carried out on a charge consisting of:

(i) 50 mmol of methyl pent-2-enoate ($P_2$)
(ii) 100 mmol of methanol (MeOH/$P_2$=2)
(iii) 0.42 mmol of dicobalt octacarbonyl ($P_2$/Co=59.5)
(iv) 6.28 mmol of isoquinoline (N/Co-7.5)
(v) 14.4 g of 1,4-dioxane (59% by weight).

The results obtained in a reaction time of two hours at 160° C. under 130 bars, using carbon monoxide containing about 2% by volume of hydrogen, were as follows:

(1) A=5.16
(2) X (%)=94.4
(3) Y (%)=79.0
(4) Z (%)=3.8

Control Experiment (m)

Example 19 was repeated, but no 1,4-dioxane was introduced.

All other conditions being equal, the results obtained were as follows:
(1) A=17.8
(2) X (%)=87.8
(3) Y (%)=63.1
(4) Z (%)=8.6

EXAMPLES 20 AND 21

Example 1 above was repeated, only the amount of 1,4-dioxane introduced being varied. The particular conditions and the results obtained are reported in Table II below.

TABLE II

| Example | 1,4-Dioxane (g) | % (by weight) | A | X (%) | Y (%) | Z (%) |
|---|---|---|---|---|---|---|
| 20 | 20.8 | 67.5 | 1.55 | 96.8 | 82.7 | 2.7 |
| 1 | 10.3 | 50.7 | 3.88 | 96.7 | 83.3 | 2.8 |
| 21 | 4.1 | 29 | 4.59 | 96.2 | 80.9 | 3.3 |

EXAMPLE 22

Using the autoclave and the procedure described above, an experiment was carried out on a charge consisting of:
(i) 50.4 mmol of methyl pent-3-enoate
(ii) 102 mmol of methanol (MeOH/$P_3$=2.02)
(iii) 2.01 mmol of dicobalt octacarbonyl ($P_3$/Co=12.5)
(iv) 16.1 mmol of 3,4-lutidine (N/CO=4.0)
(v) 10.3 g of 1,4-dioxane (46% by weight).

In a reaction time of two hours at 160° C. under 130 bars of pressure, using carbon monoxide containing 0.8% by volume of hydrogen, the following results were obtained:
(1) A=2.21
(2) X (%)=97
(3) Y (%)=76.6
(4) Z (%)=2.7

EXAMPLES 23 TO 25

Control Experiment (n)

Another series of experiments was carried out according to the following procedure:

The following materials were introduced into a 300 cm$^3$ stainless steel autoclave equipped with a magnetically driven central stirrer and electrically heated and regulated:
(i) 300 mmol of methyl pent-3-enoate
(ii) 600 mmol of methanol (MeOH/$P_3$=2)
(iii) 48 mmol of 4-picoline
(iv) 6 mmol of dicobalt octacarbonyl ($P_3$/Co=2.5; N/Co=4)

and a solvent, the type and amount of which are specified in Table III below.

The autoclave was heated to 160° C. while being swept with a mixture of carbon monoxide, hydrogen and nitrogen ($H_2$=0.22% by volume; $N_2$=5% by volume). The pressure in the autoclave was maintained at 130 bars and the flow rate of the above-mentioned mixture of gases was 40 liters/hour (converted to NTP).

Samples of the reaction mass were taken periodically and analyzed.

Table III reports the results obtained in each experiment after respective reaction times of 1 hour, 2 hours and 6 hours at the temperature indicated.

The conventions used are the same as for Examples 1 to 22 above; DC (%) is understood as meaning the degree of conversion of the methyl pent-3-enoate to products not resulting only from position isomerism of the olefinic double bond.

TABLE I(A)

| Ref. | $P_3$ mmol | MeOH mmol | DCOC mmol | MeOH/$P_3$ | $P_3$/Co | N/Co | $H_2$ (% by volume) | P bars | T °C. |
|---|---|---|---|---|---|---|---|---|---|
| a | 50.1 | 109 | 1.02 | 2.17 | 24.6 | 4 | 0 | 130 | 160 |
| b | 49.7 | 99 | 0.88 | 1.99 | 28.5 | 4.5 | 0.7 | 130 | 160 |
| c | 99.8 | 198 | 2.00 | 1.98 | 25.0 | 12 | 0.9 | 130 | 160 |
| d | 99.8 | 200 | 2.01 | 2.00 | 24.8 | 12 | 2.6 | 130 | 160 |
| e | 50.3 | 104 | 1.00 | 2.07 | 25.2 | 3.9 | 0.8 | 130 | 160 |
| 1 | 50.0 | 102 | 1.00 | 2.04 | 25.0 | 4.0 | 0.8 | 130 | 160 |
| 2 | 50.5 | 101 | 1.00 | 2.00 | 25.3 | 4.0 | 0.8 | 130 | 160 |
| 3 | 50.0 | 102 | 0.99 | 2.04 | 25.2 | 4.3 | 0.8 | 130 | 160 |
| 4 | 50.2 | 101 | 1.00 | 2.01 | 25.1 | 4.0 | 0.8 | 130 | 160 |
| 5 | 50.0 | 102 | 1.01 | 2.04 | 24.8 | 3.9 | 0.8 | 130 | 160 |
| 6 | 50.3 | 100 | 0.99 | 1.99 | 25.4 | 4.0 | 0.9 | 130 | 160 |
| 7 | 50.2 | 100 | 1.00 | 1.99 | 25.1 | 4.0 | 1.0 | 130 | 160 |
| 8 | 50.3 | 101 | 1.01 | 2.01 | 24.9 | 4.0 | 1.0 | 130 | 160 |
| 9 | 50.2 | 98 | 1.01 | 1.95 | 24.8 | 3.9 | 0.9 | 130 | 160 |
| 10 | 50.2 | 100 | 1.00 | 1.99 | 24.8 | 4.0 | 0.9 | 130 | 160 |
| 11 | 50.5 | 101 | 1.00 | 2.00 | 25.3 | 3.8 | 0.9 | 130 | 160 |
| 12 | 50 | 101 | 1.00 | 2.02 | 25.0 | 4.0 | 0.9 | 130 | 160 |
| f | 49.6 | 104 | 0.98 | 2.09 | 25.0 | 20.6 | 0.8 | 130 | 160 |
| 13 | 49.7 | 102 | 1.00 | 2.05 | 25.0 | 20.0 | 0.8 | 130 | 160 |
| g | 100 | 198 | 1.98 | 1.98 | 25.4 | 0.53 | 0.8 | 130 | 160 |
| 14 | 100 | 202 | 2.00 | 2.02 | 25.1 | 0.54 | 0.8 | 130 | 160 |
| h | 49.7 | 100 | 1.03 | 2.01 | 24.1 | 3.8 | 0.8 | 130 | 140 |
| 15 | 50.1 | 101 | 0.98 | 2.01 | 25.5 | 4.1 | 0.8 | 130 | 140 |
| i | 100 | 198 | 3.90 | 1.98 | 12.7 | 4.0 | 0.8 | 130 | 160 |
| 16 | 50 | 102 | 2.01 | 2.04 | 12.4 | 4.0 | 0.8 | 130 | 160 |
| j | 100 | 200 | 2 | 2 | 25 | 2 | 0.4 | 80 | 160 |
| 17 | 50 | 100 | 1 | 2 | 25 | 2 | 0.4 | 80 | 160 |
| k | 100 | 200 | 2 | 2 | 25 | 12 | 1 | 200 | 160 |
| 18 | 50 | 100 | 1 | 2 | 25 | 12 | 1 | 200 | 160 |

TABLE I(B)

| Ref. | SOLVENT nature | (% by weight) | t | A | X (%) | Y (%) | Z (%) |
|---|---|---|---|---|---|---|---|
| a | — | 0 | 1 | 3.7 | 95.1 | 79.4 | 4.9 |

TABLE I(B)-continued

| | SOLVENT | | | | | | |
|---|---|---|---|---|---|---|---|
| Ref. | nature | (% by weight) | t | A | X (%) | Y (%) | Z (%) |
| b | — | 0 | 1 | 10.4 | 89.0 | 74.6 | 10.4 |
| c | — | 0 | 1 | 1.9 | 94.7 | 75.5 | 4.9 |
| d | — | 0 | 1 | 3.3 | 92.5 | 74.7 | 6.8 |
| e | — | 0 | 2 | 7.9 | 92.3 | 76.4 | 7.0 |
| 1 | 1,4-dioxane | 50 | 2 | 3.9 | 96.7 | 83.3 | 2.8 |
| 2 | 1,4-dithian | 50 | 5 | 2.5 | 95.2 | 83.6 | 4.4 |
| 3 | 1,3,5-trioxane | 50 | 2 | 2.9 | 94.1 | 80.2 | 5.9 |
| 4 | 1,3,5-trioxane | 50 | 2 | 3.8 | 95.9 | 79.2 | 3.7 |
| 5 | THP | 50 | 2 | 4.8 | 93.8 | 80.7 | 5.4 |
| 6 | thianthrene | 50 | 2 | 7.7 | 94.2 | 79.4 | 5.2 |
| 7 | THT | 50 | 2 | 4.2 | 95.7 | 84.0 | 3.6 |
| 8 | benzothiazole | 50 | 2 | 1.9 | 95.0 | 80.7 | 4.8 |
| 9 | THF | 50 | 2 | 4.1 | 95.2 | 81.2 | 4.4 |
| 10 | thiophene | 54 | 2 | 2.0 | 94.7 | 82.2 | 4.6 |
| 11 | 2-MeF | 50 | 2 | 4.8 | 94.7 | 82.1 | 4.6 |
| 12 | DBF | 50 | 2 | 5.6 | 95.3 | 80.6 | 4.1 |
| f | — | 0 | 2 | 1.1 | 90.1 | 73.7 | 8.8 |
| 13 | 1,4-dioxane | 43 | 2 | 3.1 | 94.2 | 77.0 | 5.8 |
| g | — | 0 | 2 | 3.2 | 92.8 | 73.2 | 5.6 |
| 14 | 1,4-dioxane | 37 | 2 | 1.9 | 92.4 | 74 | 5.4 |
| h | — | 0 | 2 | 3.4 | 94.0 | 70.3 | 5.6 |
| 15 | 1,4-dioxane | 50 | 2 | 1.1 | 95.8 | 75.8 | 3.5 |
| i | — | 0 | 2 | 3.9 | 91.3 | 73.1 | 8.4 |
| 16 | 1,4-dioxane | 50 | 2 | 2.0 | 92.6 | 78.2 | 6.8 |
| j | — | 0 | 2 | 3.4 | 84.2 | 70.2 | 15.3 |
| 17 | THT | 50 | 2 | 1.1 | 91.9 | 78.4 | 7.5 |
| k | — | 0 | 2 | 2.4 | 96.0 | 68 | 3.4 |
| 18 | THT | 50 | 2 | 2.9 | 97.1 | 80.6 | 2.5 |

TABLE III

| Ref. | SOLVENT | Time in hours | DC (%) | X (%) | Y (%) | Z (%) |
|---|---|---|---|---|---|---|
| n | methyl isobutyl ketone | 1 | 29.8 | 92.5 | 78.2 | 7.0 |
| | 60 ml (44.6% by weight) | 2 | 53.3 | 92.6 | 78.2 | 6.9 |
| | | 6 | 97.1 | 92.2 | 77.8 | 7.4 |
| 23 | 1,4-dioxane | 1 | 23.2 | 92.8 | 79.0 | 6.8 |
| | 60 ml (50% by weight) | 2 hours 20 min | 47.4 | 93.1 | 79.8 | 6.4 |
| | | 6 | 93.6 | 92.2 | 79.2 | 6.7 |
| 24 | thiophene | 1 | 16.6 | 93.9 | 80.8 | 5.8 |
| | 60 ml (51% by weight) | 2 hours 10 min | 31.3 | 94.2 | 81.2 | 5.3 |
| | | 6 | 72.5 | 94.1 | 80.6 | 5.4 |
| 25 | tetrahydrothiophene | 1 | 18.8 | 95.3 | 83.9 | 4.3 |
| | 60 ml (49% by weight) | 2 | 36.1 | 95.2 | 83.5 | 4.4 |
| | | 6 | 84.7 | 95.1 | 83.3 | 4.4 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a linear carboxylic acid ester, comprising reacting an alcohol and carbon monoxide with a monoolefin, in the presence of cobalt and a tertiary nitrogen base, and in a reaction solvent which comprises a 5- or 6-membered monoheterocycle containing from 1 to 3 identical or different, non-adjacent oxygen or divalent sulfur heteroatoms, wherein said heterocycle can also contain from one to two carbon-carbon double bonds.

2. The process as defined by claim 1, said reaction also being carried out in the presence of hydrogen.

3. The process as defined by claim 1, wherein said monoheterocycle reaction solvent comprises only sulfur heteroatoms.

4. The process as defined by claim 1, wherein said monoheterocycle reaction solvent is 6-membered and at least two of the heteroatoms thereof are the same and are either oxygen or divalent sulfur.

5. The process as defined by claim 1, wherein said monoheterocycle reaction solvent comprises thiophene, tetrahydrothiophene, furan, tetrahydrofuran, 1,4-dioxane, 1,4-dithian or trithian.

6. The process as defined by claim 1, wherein said monoheterocycle reaction solvent comprises at least 20% by weight of the initial reaction mixture.

7. The process as defined by claim 6, wherein said monoheterocycle reaction solvent comprises from 30 to 60% by weight of the initial reaction mixture.

8. The process as defined by claim 2, the amount of hydrogen present comprising up to 3% by volume of the carbon monoxide.

9. The process as defined by claim 1, wherein the atomic ratio N/Co ranges from 1 to 50.

10. The process as defined by claim 9, wherein the reaction temperature ranges from 120° to 200° C.

11. The process as defined by claim 10, wherein the reaction pressure ranges from 50 to 1,000 bars.

12. The process as defined by claim 1, wherein the starting material monoolefin comprises an alkyl pentenoate.

13. The process as defined by claim 1, wherein said tertiary nitrogen base has a $pK_a$ ranging from 3 to 10.

14. The process as defined by claim 1, wherein the starting material monoolefin has the formula $R_1CH=CHR_2$, wherein $R_2$ is hydrogen, an alkyl radical having up to 20 carbon atoms, or a substituted such alkyl radical bearing one or two chlorine or $C_1-C_4$ alkoxy substituents, $R_1$ is $R_2$ or one of the radicals $-(CH_2)_pCOOH$, $-(CH_2)_pCOOR_3$ or $-(CH_2)_pCN$, in which p is an integer ranging from 0 to 6 and $R_3$ is an alkyl radical having up to 12 carbon atoms or a substituted such alkyl radical wherein one or two of the methylene groups thereof bears an alkyl substituent having up to 4 carbon atoms, and $R_1$ and $R_2$ may together form a single divalent radical $-(CH_2)_q$, in which q is an integer ranging from 3 to 6 or a substituted such radical bearing one or two alkyl substituents having up to 4 carbon atoms.

15. The process as defined by claim 14, wherein the starting material alcohol has the formula R—OH, wherein R is an alkyl radical having up to 12 carbon atoms, a substituted such alkyl radical bearing one or two hydroxyl substituents, a cycloalkyl radical having from 5 to 7 carbon atoms, an aralkyl radical having from 7 to 12 carbon atoms, or a phenyl radical.

16. The process as defined by claim 1, wherein said heterocyclic ring comprises from 1 to 4 carbon atoms substituted by one or two groups which do not interfere with the other components of the reaction medium, the size of which is not large enough to create excessive steric hindrance around any heteroatom of the ring, said groups having the formula R'—Y—, wherein R' represents an alkyl, aralkyl or aryl radical having from 1 to 10 carbon atoms and Y represents a valence bond, an oxygen atom, a sulfur atom or a carbonyl group.

17. The process as defined by claim 1, wherein one or two pairs of adjacent carbon atoms of the heterocyclic ring can each be included in a benzene or naphthalene nucleus joined to the heterocyclic ring.

18. A process for the preparation of a linear carboxylic acid ester, comprising reacting an alcohol and carbon monoxide with a monoolefin, in the presence of cobalt and a tertiary nitrogen base, and in a reaction solvent which comprises a 6-membered monoheterocycle containing 2 to 3 identical, non-adjacent oxygen or divalent sulfur heteroatoms, wherein said heterocycle can also contain one or two carbon-carbon double bonds.

19. A process for the preparation of a linear carboxylic acid ester, comprising reacting an alcohol and carbon monoxide with a monoolefin, in the presence of cobalt and a tertiary nitrogen base, and in a reaction solvent which comprises a 5-membered monoheterocycle containing from 1 to 3 identical or different, non-adjacent oxygen or divalent sulfur heteroatoms, wherein said heterocycle can also contain one or two carbon-carbon double bonds and a nitrogen heteroatom separated from an oxygen or sulfur heteroatom by at least one ring carbon atom and linked to one of the adjacent carbon atoms by a double bond.

20. The process as defined by claim 19, wherein said monoheterocycle is oxazole or thiazole.

* * * * *